United States Patent [19]

Sagai et al.

[11] Patent Number: 5,043,279

[45] Date of Patent: Aug. 27, 1991

[54] DNA ENCODING A BACILLUS CREATINASE

[75] Inventors: Hitoshi Sagai; Harumi Masujima, both of Mishima; Shigeru Ikuta; Koji Suzuki, both of Shizuoka, all of Japan

[73] Assignee: Toyo Jozo Company, Ltd., Shizuoka, Japan

[21] Appl. No.: 225,770

[22] Filed: Jul. 29, 1988

[30] Foreign Application Priority Data

Aug. 4, 1987 [JP] Japan ................. 62-195014

[51] Int. Cl.$^5$ ............ G12P 21/02; G12P 19/34; C12N 15/00; C12N 7/00; C12N 1/21; C12N 15/70; C12N 9/78; C07H 15/12; C07K 3/00
[52] U.S. Cl. .................. 435/227; 435/91; 435/172.3; 435/235.1; 435/320.1; 435/252.3; 435/252.33; 435/69.1; 536/27; 530/350; 935/19; 935/29; 935/41; 935/56; 935/60; 935/73; 935/82
[58] Field of Search ............ 435/69.1, 91, 172.3, 435/252.31, 252.33; 536/27; 530/350; 935/19, 29, 41, 56, 60, 73, 82

[56] References Cited

U.S. PATENT DOCUMENTS 4,420,562 12/1983 Ikuta et al. ................. 435/227

FOREIGN PATENT DOCUMENTS 0187138 7/1986 European Pat. Off. .
0291055 11/1988 European Pat. Off. .

OTHER PUBLICATIONS

Derwent Abstract of Netherlands Patent 7205996.
Derwent Abstract of Netherlands Patent 7205997.
Derwent Abstract of Japan Patent 1067-484.
Derwent Abstract of Japan Patent 1067-485.
Derwent Abstract of European Patent 187-138.
Molecular Cloning: A Laboratory Manual Cold Spring Harbor Laboratory, CSA N.Y. (1982) pp. 310-328.

Primary Examiner—Richard A. Schwartz
Assistant Examiner—Joan Ellis
Attorney, Agent, or Firm—Oblon, Spivak, McClelland, Maier & Neustadt

[57] ABSTRACT

The disclosure is made on a polydeoxyribonucleic acid having a base sequence encoding an amino acid sequence of a polypeptide which is a creatinase derived from a creatinase-producing microorganism belonging to the genus of Bacillus. The bsae sequence of the creatinase gene DNA and amino acid sequence of the creatinase have been clarified. The transformant having this polydeoxyribonucleic acid as well as a process for preparing the creatinase at a high productivity with the application of genetic engineering technique are disclosed.

9 Claims, 5 Drawing Sheets

FIG. 2-1

```
                                                          60
ATGCAACAAATCACAGATCTTGAAAGAACAAAGATTTTACAAAACGGCGGGGAGAAAGTA

120
AAGCCCACTTTTTCAAAAGAGGAAATGACACGCCGCAATACCCGTTTACGCGAGTATATG

180
GCGAAGGCCGGAATCGATGCTGTTATGTTCACTTCTTACCATAATATCAACTATTACAGC

240
GACTTTTTATATACATCATTCAACAGATCGTATGCGCTCGTCGTCACTCAGGACAAGCAT

300
GTGACTGTAAGCGCAAACATTGATGCCGGCATGCCGTGGAGACGCAGCTTTGACGAGAAT

360
ATTGTTTACACAGACTGGAAAAGAGACAACTTTCTTTATGCCGTGAAAAAGGTATTAAAT

420
GAGGGAGGCTTCTCCAGCGGCCGTCTCGGTGTAGAAAATGATCATATGACGCTGGATTTA

480
CGGCGCCAAGTGCAGGATGCCCTGCCAAACACAGAGCTTGTGGACGTTTCCCAGGCGGTG

540
ATGGGGCATCGGATGTTTAAGTCTGACGAGGAAATTGATTTGATTAAAAATGGAGCCCGT

600
ATTGCAGATATCGGCGGAGCGGCCGTTGTCGAAGCGATTCGCGAAGGCGTACCGGAATAC

660
GAAGTGGCGCTGCATGGGACAGAAGCAATGGTACGCGAAATTGCCCGTACGTACCCGCAC

720
GCTGAACTTCGGGACACGTGGATTTGGTTTCAATCCGGCATTAATACGGACGGCGCTCAC

780
AACTGGGCGACTTCCCGCAAGCTGCAGCGAGGAGATATTTTGAGCCTAAACTGCTTCCCG

840
ATGATCGCTGGTTACTATACGGCACTTGAGCGCACGTTGTTCTTGGAAGAAGTGTCTGAC

900
CGCCATCTTGAACTGTGGGAAATCAACTGTAAAGTGCATAGACGCGGCCTTGAACTGATC

960
AAGCCAGGGGCTAGATGTATGGATATCGCCGCTGAATTAAATGAGATCTACCGCGAGCAC

1020
GACTTGTTGGCGAACCGGACGTTCGGTTACGGACACTCATTCGGCGTACTGAGCCACTAT
```

FIG. 2-2

```
                                                                    1080
TACGGACGTGAGGCTGGACTGGAGCTGCGGGAAGATATCGAAACAGTGTTGGAGCCGGGC

1140
ATGGTTGTGTCCATGGAACCAATGATCATGATTCCAGAGGGAGAGCCGGGAGCGGGCGGT

1200
TACCGTGAGCACGACATCCTCGTTATTAGCGAGAACGGGACAGAGAATATCACTAAGTTC

1260
CCATTCGGTCCGGAGCATAACATTATTAAAAAG
```

FIG. 3-1

```
         10        20        30        40        50        60
ATGCAACAAATCACAGATCTTGAAAGAACAAAGATTTTACAAAACGGCGGGGAGAAAGTA
MetGlnGlnIleThrAspLeuGluArgThrLysIleLeuGlnAsnGlyGlyGluLysVal 70        80        90       100       110       120
AAGCCCACTTTTTCAAAAGAGGAAATGACACGCCGCAATACCCGTTTACGCGAGTATATG
LysProThrPheSerLysGluGluMetThrArgArgAsnThrArgLeuArgGluTyrMet 130       140       150       160       170       180
GCGAAGGCCGGAATCGATGCTGTTATGTTCACTTCTTACCATAATATCAACTATTACAGC
AlaLysAlaGlyIleAspAlaValMetPheThrSerTyrHisAsnIleAsnTyrTyrSer 190       200       210       220       230       240
GACTTTTTATATACATCATTCAACAGATCGTATGCGCTCGTCGTCACTCAGGACAAGCAT
AspPheLeuTyrThrSerPheAsnArgSerTyrAlaLeuValValThrGlnAspLysHis 250       260       270       280       290       300
GTGACTGTAAGCGCAAACATTGATGCCGGCATGCCGTGGAGACGCAGCTTTGACGAGAAT
ValThrValSerAlaAsnIleAspAlaGlyMetProTrpArgArgSerPheAspGluAsn 310       320       330       340       350       360
ATTGTTTACACAGACTGGAAAAGAGACAACTTTCTTTATGCCGTGAAAAAGGTATTAAAT
IleValTyrThrAspTrpLysArgAspAsnPheLeuTyrAlaValLysLysValLeuAsn 370       380       390       400       410       420
GAGGGAGGCTTCTCCAGCGGCCGTCTCGGTGTAGAAAATGATCATATGACGCTGGATTTA
GluGlyGlyPheSerSerGlyArgLeuGlyValGluAsnAspHisMetThrLeuAspLeu 430       440       450       460       470       480
CGGCGCCAAGTGCAGGATGCCCTGCCAAACACAGAGCTTGTGGACGTTTCCCAGGCGGTG
ArgArgGlnValGlnAspAlaLeuProAsnThrGluLeuValAspValSerGlnAlaVal 490       500       510       520       530       540
ATGGGCATCGGATGTTTAAGTCTGACGAGGAAATTGATTTGATTAAAAATGGAGCCCGT
MetGlyHisArgMetPheLysSerAspGluGluIleAspLeuIleLysAsnGlyAlaArg 550       560       570       580       590       600
ATTGCAGATATCGGCGGAGCGGCCGTTGTCGAAGCGATTCGCGAAGGCGTACCGGAATAC
IleAlaAspIleGlyGlyAlaAlaValValGluAlaIleArgGluGlyValProGluTyr 610       620       630       640       650       660
GAAGTGGCGCTGCATGGGACAGAAGCAATGGTACGCGAAATTGCCCGTACGTACCCGCAC
GluValAlaLeuHisGlyThrGluAlaMetValArgGluIleAlaArgThrTyrProHis 670       680       690       700       710       720
GCTGAACTTCGGGACACGTGGATTTGGTTTCAATCCGGCATTAATACGGACGGCGCTCAC
AlaGluLeuArgAspThrTrpIleTrpPheGlnSerGlyIleAsnThrAspGlyAlaHis 730       740       750       760       770       780
AACTGGGCGACTTCCCGCAAGCTGCAGCGAGGAGATATTTTGAGCCTAAACTGCTTCCCG
AsnTrpAlaThrSerArgLysLeuGlnArgGlyAspIleLeuSerLeuAsnCysPhePro
```

FIG. 3-2

```
          790       800       810       820       830       840
ATGATCGCTGGTTACTATACGGCACTTGAGCGCACGTTGTTCTTGGAAGAAGTGTCTGAC
MetIleAlaGlyTyrTyrThrAlaLeuGluArgThrLeuPheLeuGluGluValSerAsp 850       860       870       880       890       900
CGCCATCTTGAACTGTGGGAAATCAACTGTAAAGTGCATAGACGCGGCCTTGAACTGATC
ArgHisLeuGluLeuTrpGluIleAsnCysLysValHisArgArgGlyLeuGluLeuIle 910       920       930       940       950       960
AAGCCAGGGGCTAGATGTATGGATATCGCCGCTGAATTAAATGAGATCTACCGCGAGCAC
LysProGlyAlaArgCysMetAspIleAlaAlaGluLeuAsnGluIleTyrArgGluHis 970       980       990      1000      1010      1020
GACTTGTTGGCGAACCGGACGTTCGGTTACGGACACTCATTCGGCGTACTGAGCCACTAT
AspLeuLeuAlaAsnArgThrPheGlyTyrGlyHisSerPheGlyValLeuSerHisTyr 1030      1040      1050      1060      1070      1080
TACGGACGTGAGGCTGGACTGGAGCTGCGGGAAGATATCGAAACAGTGTTGGAGCCGGGC
TyrGlyArgGluAlaGlyLeuGluLeuArgGluAspIleGluThrValLeuGluProGly 1090      1100      1110      1120      1130      1140
ATGGTTGTGTCCATGGAACCAATGATCATGATTCCAGAGGGAGAGCCGGGAGCGGGCGGT
MetValValSerMetGluProMetIleMetIleProGluGlyGluProGlyAlaGlyGly 1150      1160      1170      1180      1190      1200
TACCGTGAGCACGACATCCTCGTTATTAGCGAGAACGGGACAGAGAATATCACTAAGTTC
TyrArgGluHisAspIleLeuValIleSerGluAsnGlyThrGluAsnIleThrLysPhe 1210      1220      1230
CCATTCGGTCCGGAGCATAACATTATTAAAAAG
ProPheGlyProGluHisAsnIleIleLysLys
```

DNA ENCODING A BACILLUS CREATINASE

BACKGROUND OF THE INVENTION

1. Field of the Invention

The present invention relates to a novel polydeoxyribonucleic acid having a genetic information of creatinase.

The invention also relates to a transformant having said polydeoxyribonucleic acid, and to the creatinase and a process for preparing the same through expression by the transformant of the genetic information of said polydeoxyribonucleic acid.

2. Description of the Background

Creatinase is a enzyme which catalyzes the reaction of creatine and water to produce urea and sarcosine. This substance has been known to exist in microorganisms belonging to genera of *Pseudomonas Journal of General Microbiology*, 14, 351,(1956)], *Artherobactor* [*Molecular & Cellular Biochemistry*, 3, 9, (1974)], *Alcaligenes*, . *Penicilium* (Japanese Patent Publication No. 7674/1981), *Flavobacterium*, *Micrococcus*, *Colinebacterium* (Japanese Patent Publication No. 8395/1977), *Bacillus* (Japanese Patent Publication No. 17465/1986), *Actinobacillus* (Japanese Patent Laid-open No. 67484/1981), and *Acinetobactor* (Japanese Patent Laid-open No. 67485/1981). Also, creatinase derived from *Pseudomonas cutida* by the use of genetic engineering technology has been reported.

Since creatinase is a hydrogenase having creatine as its substrate, it can be used for quantitation of creatine existing in a body fluid such as serum. It can also be utilized, through measurement of the quantity of creatine produced in the creatinine-creatinase creatine-producing system, for quantitation of various substances which are the substrates of enzymes affecting the creatine producing system as well as for the determination of enzymatic activities involved in the creatine-producing system. Creatinase is thus a very important reagent for use not only in laboratory experiment but also in clinical diagonosis.

Creatinase-producing microorganisms reported heretofore which are utilized without recourse to genetic engineering technique yield only a poor creatinase-producing efficiency so that the use of an enzyme-inducing substance such as creatine or the like which can help producing creatinase has been indispensable. This renders the cost of the creatinase production expensive. In addition, according to this method removal of other types of enzymes, such as creatininase or the like, which may be present together with creatinase, is very difficult. The cost of purification to obtain a high purity creatinase makes the overall production cost even higher. Thus, the use of these creatinase-producing microorganisms have not always been effective and convenient route for providing creatinase as reagents for abundant use in laboratory experiment or clinical diagonosis.

The creatinase derived from creatinase-producing microorganisms belonging to the genus of Bacillus also requires the addition of an expensive enzyme-inducing substance in the course of its preparation. In addition, there has been no report on the detailed chemical structure of the polypeptide constituting this enzyme.

The present inventors have undertaken extensive studies in order to improve the productivity of this creatinase, and have succeeded in obtaining the gene of this creatinase and further in clarifying its primary structural analysis. Further, the inventors have established a method for preparing the creatinase at a high productivity with the application of genetic engineering technique.

In addition, through analysis of the DNA sequence of the creatinase gene induced from the creatinase-producing microorganisms belonging to the genus of Bacillus the inventors have found that the enzyme possessed amino acid sequence and base sequence structures which are quite different from those of creatinase produced by conventionally known genetic engineering technique. The inventors also found that proteins obtained exhibited unexpectedly excellent creatinase activities. These findings have led to the completion of this invention.

The novel process for preparing creatinase according to this invention does not require the use of an expensive enzyme-inducing substance such as creatine in the course of creatinase production, and is thus a commercially advantageous process.

SUMMARY OF THE INVENTION

Accordingly, an object of this invention is to provide a polydeoxyribonucleic acid having a base sequence encoding an amino acid sequence of a polypeptide which is the creatinase derived from a creatinase-producing microorganism belonging to the genus of Bacillus or of a polypeptide having said creatinase as its constituent.

Another object of this invention is to provide a transformant having this polydeoxyribonucleic acid.

A further object is to provide a polypeptide comprising a creatinase having an amino acid sequence starting from the N-terminal of the following formula, or a polypeptide having such creatinase as its constituent:

A—Gln Gln Ile Thr Asp Leu Glu Arg Thr (I)
10
Lys Ile Leu Gln Asn Gly Gly Glu Lys Val
20
Lys Pro Thr Phe Ser Lys Glu Glu Met Thr
30
Arg Arg Asn Thr Arg Leu Arg Glu Tyr Met
40
Ala Lys Ala Gly Ile Asp Ala Val Met Phe
50
Thr Ser Tyr His Asn Ile Asn Tyr Tyr Ser
60
Asp Phe Leu Tyr Thr Ser Phe Asn Arg Ser
70
Tyr Ala Leu Val Val Thr Gln Asp Lys His
80
Val Thr Val Ser Ala Asn Ile Asp Ala Gly
90
Met Pro Trp Arg Arg Ser Phe Asp Glu Asn
100
Ile Val Tyr Thr Asp Trp Lys Arg Asp Asn
110
Phe Leu Tyr Ala Val Lys Lys Val Leu Asn
120
Glu Gly Gly Phe Ser Ser Gly Arg Leu Gly
130
Val Glu Asn Asp His Met Thr Leu Asp Leu
140
Arg Arg Gln Val Gln Asp Ala Leu Pro Asn
150
Thr Glu Leu Val Asp Val Ser Gln Ala Val
160
Met Gly His Arg Met Phe Lys Ser Asp Glu
170
Glu Ile Asp Leu Ile Lys Asn Gly Ala Arg
180
Ile Ala Asp Ile Gly Gly Ala Ala Val Val

-continued

```
190
Glu Ala Ile Arg Glu Gly Val Pro Glu Tyr
200
Glu Val Ala Leu His Gly Thr Glu Ala Met
210
Val Arg Glu Ile Ala Arg Thr Tyr Pro His
220
Ala Glu Leu Arg Asp Thr Trp Ile Trp Phe
230
Gln Ser Gly Ile Asn Thr Asp Gly Ala His
240
Asn Trp Ala Thr Ser Arg Lys Leu Gln Arg
250
Gly Asp Ile Leu Ser Leu Asn Cys Phe Pro
260
Met Ile Ala Gly Tyr Tyr Thr Ala Leu Glu
270
Arg Thr Leu Phe Leu Glu Glu Val Ser Asp
280
Arg His Leu Glu Leu Trp Glu Ile Asn Cys
290
Lys Val His Arg Arg Gly Leu Glu Leu Ile
300
Lys Pro Gly Ala Arg Cys Met Asp Ile Ala
310
Ala Glu Leu Asn Glu Ile Tyr Arg Glu His
320
Asp Leu Leu Ala Asn Arg Thr Phe Gly Tyr
330
Gly His Ser Phe Gly Val Leu Ser His Tyr
340
Tyr Gly Arg Glu Ala Gly Leu Glu Leu Arg
350
Glu Asp Ile Glu Thr Val Leu Glu Pro Gly
360
Met Val Val Ser Met Glu Pro Met Ile Met
370
ILe Pro Glu Gly Glu Pro Gly Ala Gly Gly
380
Tyr Arg Glu His Asp Ile Leu Val Ile Ser
390
Glu Asn Gly Thr Glu Asn Ile Thr Lys Phe
400
Pro Phe Gly Pro Glu His Asn Ile Ile Lys
410
Lys—B
``` wherein A represents an amino acid residue, an acetyl group, or a hydrogen atom and B represents an amino acid residue or —OH or $NH_2$.

A still further object of this invention is to provide a process for preparing creatinase comprising:

inserting a polydeoxyribonucleic acid which is a creatinase gene derived from a creatinase-producing microorganism belonging to the genus of Bacillus or a polydeoxyribonucleic acid having said creatinase gene as its constituent into a expression vector thus producing a recombinant DNA, producing a transformant by introducing said recombinant DNA into a host microorganism and culturing said transformant to cause the transformant to manifest the genetic information of said polydeoxyribonucleic acid, and collecting the polypeptide of said creatinase or the polypeptide having said creatinase as it constituent.

Other objects, features and advantages of the invention will hereinafter become more readily apparent from the following description.

BRIEF DESCRIPTION OF THE DRAWINGS

FIGS. 2-1 and 2-2 show the base sequence of the creatinase gene DNA (from 5' through 3'), and FIGS. 3-1 and 3-2 show the amino acid sequence of the translational product produced therefrom.

DETAILED DESCRIPTION OF THE INVENTION AND PREFERRED EMBODIMENTS

Figure 1:
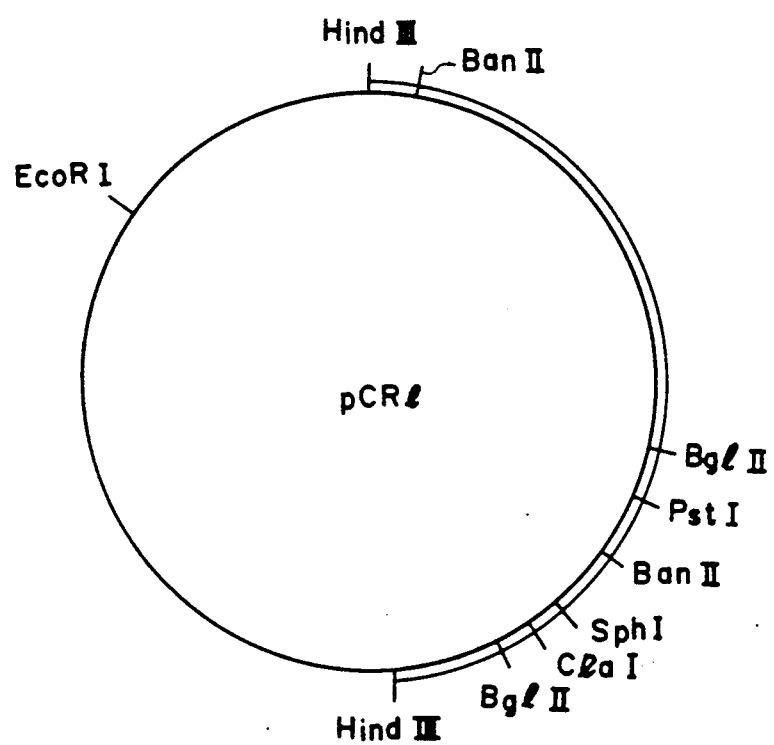
FIG. 1 is a schematic drawing showing the construction of pCR1 vector, indicating sites of incision of the pCR1 vector with the use of restriction endonucleases EcoR I, Hind III, Ban II, Bgl II, Pst I, Sph I, and Cla I.

In the polypeptide of formula (I), the amino acid residue represented by A may be one or more amino acid residues. Preferred examples of A are a hydrogen atom, a methionine, or a signal polypeptide. The group represented by B ma be an acid amide or one or more amino acid residues.

A polydeoxyribonucleic acid which codes for a creatinase gene acting as a catalyst in the reaction of creatine and water to produce urea and sarcosine, or a polydeoxyribonucleic acid having said gene as its constituent, may be any polydeoxyribonucleic acid so long as it contains said creatinase gene itself. Given as examples of said creatinase gen itself are creatine represented by the following formula (II) starting from the N-terminal:

```
    Gln Gln Ile Thr Asp Leu Glu Arg Thr        (II)
    10
    Lys Ile Leu Gln Asn Gly Gly Glu Lys Val
    20
    Lys Pro Thr Phe Ser Lys Glu Glu Met Thr
    30
    Arg Arg Asn Thr Arg Leu Arg Glu Tyr Met
    40
    Ala Lys Ala Gly Ile Asp Ala Val Met Phe
    50
    Thr Ser Tyr His Asn Ile Asn Tyr Tyr Ser
    60
    Asp Phe Leu Tyr Thr Ser Phe Asn Arg Ser
    70
    Tyr Ala Leu Val Val Thr Gln Asp Lys His
    80
    Val Thr Val Ser Ala Asn Ile Asp Ala Gly
    90
    Met Pro Trp Arg Arg Ser Phe Asp Glu Asn
    100
    Ile Val Tyr Thr Asp Trp Lys Arg Asp Asn
    110
    Phe Leu Tyr Ala Val Lys Lys Val Leu Asn
    120
    Glu Gly Gly Phe Ser Ser Gly Arg Leu Gly
    130
    Val Glu Asn Asp His Met Thr Leu Asp Leu
    140
    Arg Arg Gln Val Gln Asp Ala Leu Pro Asn
    150
    Thr Glu Leu Val Asp Val Ser Gln Ala Val
    160
    Met Gly His Arg Met Phe Lys Ser Asp Glu
    170
    Glu Ile Asp Leu Ile Lys Asn Gly Ala Arg
    180
    Ile Ala Asp Ile Gly Gly Ala Ala Val Val
    190
    Glu Ala Ile Arg Glu Gly Val Pro Glu Tyr
    200
    Glu Val Ala Leu His Gly Thr Glu Ala Met
    210
    Val Arg Glu Ile Ala Arg Thr Tyr Pro His
    220
    Ala Glu Leu Arg Asp Thr Trp Ile Trp Phe
    230
    Gln Ser Gly Ile Asn Thr Asp Gly Ala His
    240
    Asn Trp Ala Thr Ser Arg Lys Leu Gln Arg
    250
    Gly Asp Ile Leu Ser Leu Asn Cys Phe Pro
    260
    Met Ile Ala Gly Tyr Tyr Thr Ala Leu Glu
```

-continued

```
270
Arg Thr Leu Phe Leu Glu Glu Val Ser Asp
280
Arg His Leu Glu Leu Trp Glu Ile Asn Cys
290
Lys Val His Arg Arg Gly Leu Glu Leu Ile
300
Lys Pro Gly Ala Arg Cys Met Asp Ile Ala
310
Ala Glu Leu Asn Glu Ile Tyr Arg Glu His
320
Asp Leu Leu Ala Asn Arg Thr Phe Gly Tyr
330
Gly His Ser Phe Gly Val Leu Ser His Tyr
340
Tyr Gly Arg Glu Ala Gly Leu Glu Leu Arg
350
Glu Asp Ile Glu Thr Val Leu Glu Pro Gly
360
Met Val Val Ser Met Glu Pro Met Ile Met
370
Ile Pro Glu Gly Glu Pro Gly Ala Gly Gly
380
Tyr Arg Glu His Asp Ile Leu Val Ile Ser
390
Glu Asn Gly Thr Glu Asn Ile Thr Lys Phe
400
Pro Phe Gly Pro Glu His Asn Ile Ile Lys
410
Lys
``` as well as polydeoxyribonucleic acids having a base sequence encoding an amino acid sequence of a polypeptide comprising creatinase which catalyzes the reaction of creatine and water to produce urea and saccosine. The polydeoxyribonucleic acid can be any polydeoxyribonucleic acid so long as the same possesses any codon among several codons corresponding to each of the amino acids constituting the amino acid sequence of (II) of the creatinase polypeptide. It may also be a polydeoxyribonucleic acid having at its 5'-end one or more codons other than a nonsense codon and/or at its 3'-end one or more codons. A typical example of such polydeoxyribonucleic acid is the one having a base sequence represented starting from the 5'-end by the formula (III):

```
X—CAA CAA ATC ACA GAT CTT GAA AGA ACA      (III)
30
AAG ATT TTA CAA AAC GGC GGG GAG AAA GTA
60
AAG CCC ACT TTT TCA AAA GAG GAA ATG ACA
90
CGC CGC AAT ACC CGT TTA CGC GAG TAT ATG
120
GCG AAG GCC GGA ATC GAT GCT GTT ATG TTC
150
ACT TCT TAC CAT AAT ATC AAC TAT TAC AGC
180
GAC TTT TTA TAT ACA TCA TTC AAC AGA TCG
210
TAT GCG CTC GTC GTC ACT CAG GAC AAG CAT
240
GTG ACT GTA AGC GCA AAC ATT GAT GCC GGC
270
ATG CCG TGG AGA CGC AGC TTT GAC GAG AAT
300
ATT GTT TAC ACA GAC TGG AAA AGA GAC AAC
330
TTT CTT TAT GCC GTG AAA AAG GTA TTA AAT
360
GAG GGA GGC TTC TCC AGC GGC CGT CTC GGT
390
GTA GAA AAT GAT CAT ATG ACG CTG GAT TTA
420
CGG CGC CAA GTG CAG GAT GCC CTG CCA AAC
450
ACA GAG CTT GTG GAC GTT TCC CAG GCG GTF
480
ATG GGG CAT CGG ATG TTT AAG TCT GAC GAG
510
GAA ATT GAT TTG ATT AAA AAT GGA GCC CGT
540
ATT GCA GAT ATC GGC GGA GCG GCC GTT GTC
570
GAA GCG ATT CGC GAA GGC GTA CCG GAA TAC
600
GAA GTG GCG CTG CAT GGG ACA GAA GCA ATG
630
GTA CGC GAA ATT GCC CGT ACG TAC CCG CAC
660
GCT GAA CTT CGG GAC ACG TGG ATT TGG TTT
690
CAA TCC GGC ATT AAT ACG GAC GGC GCT CAC
720
AAC TGG GCG ACT TCC CGC AAG CTG CAG CGA
750
GGA GAT ATT TTG AGC CTA AAC TGC TTC CCG
780
ATG ATC GCT GGT TAC TAT ACG GCA CTT GAG
810
CGC ACG TTG TTC TTG GAA GAA GTG TCT GAC
840
CGC CAT CTT GAA CTG TGG GAA ATC AAC TGT
870
AAA GTG CAT AGA CGC GGC CTT GAA CTG ATC
900
AAG CCA GGG GCT AGA TGT ATG GAT ATC GCC
930
GCT GAA TTA AAT GAG ATC TAC CGC GAG CAC
960
GAC TTG TTG GCG AAC CGG ACG TTC GGT TAC
990
GGA CAC TCA TTC GGC GTA CTG AGC CAC TAT
1020
TAC GGA CGT GAG GCT GGA CTG GAG CTG CGG
1050
GAA GAT ATC GAA ACA GTG TTG GAG CCG GGC
1080
ATG GTT GTG TCC ATG GAA CCA ATG ATC ATG
1110
ATT CCA GAG GGA GAG CCG GGA GCG GGC GGT
1140
TAC CGT GAG CAC GAC ATC CTC GTT ATT AGC
1170
GAG AAC GGG ACA GAG AAT ATC ACT AAG TTC
1200
CCA TTC GGT CCG GAG CAT AAC ATT ATT AAA
1230
AAG—Y
``` in which X represents a codon other than TAA, TAG and TGA, or a hydrogen atom, and Y stands for a codon or a hydrogen atom.

Concerning the base sequence of formula (III), the codon represented by X may be any codon so long as the same codes for an amino acid. In addition, X may possess at its 5'-end one or more codons encoding amino acids. Preferable examples of X are ATG or a polydeoxyribonuclei acid corresponding to a signal peptide.

The codon represented by Y can be any codon selected from translation termination codons and codons encoding an amino acid. Y may possess at its 3'-end one or more codons encoding amino acids, provided that in this case it is desirable that a translation termination codon be provided at the 3'-end of these codons.

A polydeoxyribonucleic acid having a creatinase gene as its constituent, a polydeoxyribonucleic acid which is a gene having a base sequence encoding the amino acid sequence of formula (II), or a polydeoxyribonucleic acid represented by formula (III), can be prepared by the process comprising the following steps.

A DNA of a creatinase-producing microorganism which is a donor of a creatinase gene is first separated and purified, followed by treatment with ultrasonic wave or with a restriction endoneuclease. This DNA and a digested linear expression vector DNA are joined with a DNA ligase blunt or cohesive ends of the two DNAs to form a closed circle. The recombinant DNA vector thus obtained is introduced into a reproducible host microorganism. Microorganisms having said recombinant DNA vector collected by means of a screening using the vector marker and the creatinase activity as indicators ar cultured. Said recombinant DNA vector is then separated from the cultured microorganisms and purified, from which the creatinase gene polydeoxyribonucleic acid is collected.

Any creatinase-producing microorganisms can be used as a creatinase gene-donating microorganism for the purpose of this invention. An example is Bacillus SP B-0618 strain (FERM BP-0750) disclosed in Japanese Patent Publication No. 17465/1986.

Transformed microorganisms derived from the genus of Bacillus, to which creatinase-producing capability was provided by the use of genetic engineering technique, can also be employed as a creatinase gene-donating microorganism.

The method of collecting a DNA induced by the gene-donating microorganism is now exemplarily illustrated. Any one of the above-mentioned gene-donating microorganisms is first cultured in a liquid culture medium under aeration for 1 to 3 days. The broth thus cultured is subjected to centrifugation to collect the microorganism, which is then lysed to produce a bacteriolysis containing a creatinase gene. Treatment with a cell wall lysing enzyme such as lysozyme or $\beta$-glucanase is used for the bacteriolysis, in combination, as required, with other enzyme such as protease or a surface active agent such as sodium laurylsulfate. In addition, physical digestion of cell walls by means of freeze-thawing or French press, for example, may be employed together with the bacteriolysis.

Conventional methods of purification, including, for example, phenol extraction, protease treatment, ribonuclease treatment, precipitation from alcohol, and centrifugation, can be applied either independently or in combination to the separation and purification of DNA from the bacteriolysis.

Digestion of the DNA of the microorganism thus separated and purified can be carried out by means of treatment with ultrasonic wave or a restriction endoneuclease, for instance. In order to ensure easy joining of the DNA fragments and the vector DNA, however, the use of a restriction endoneuclease is preferable, especially those having an activity to a specific nucleotide sequences such as EcoR I, Hind III, BamH I, or BamH II.

Desirable vectors employed are those reconstructed for use as a genetic recombinant DNA through an artificial treatment of a phage or a plasmid DNA which is capable of growing autonomously in host bacterial cells.

In case where *Escherichia coli* is used as a host microorganism, for example, λgt.λC, λgt.λB, or the like is used as a phage.

As a plasmid, pBR322, pBR325, pACYC184, pUC12, pUC13, pUC18, pUC19, or the like is used when *Escherichia coli* is the host microorganism, pUB110, pC194, or the like is used when *Bacillus subtillis* is the host microorganism, and YRp7, pYC1, YEp13, pJDB, YIp1, or the like is used when *Saccharomyces cerevisiae* is the host microorganism. In addition, suttlevectors may be employed, which can autonomously grow in host bacterial cells of either or both of Gram-positive and Gram-negative microorganism, for instance, in either or both of *Escherichia coli* and *Saccharomyces cerevisiae*. These vectors are desirably digested into vector fragments by the use of the same restriction endoneuclease as that used in breaking the above-mentioned creatinase gene-donating microorganism DNA.

Conventional method of using DNA ligase can be employed for joining the bacterial DNA and the vector fragment. For instance, the cohesive end of the bacterial DNA and that of the vector fragment are first annealed, and then a recombinant DNA of the bacterial DNA and the vector fragment can be prepared by the action of a suitable DNA ligase. If required, the annealed bacterial DNA—vector fragment is introduced into the host microorganism to produce the recombinant DNA with the aid of in vivo DNA ligase.

Any microorganisms can be used as host bacteria, which allow autonomic and stable growth of the recombinant DNA and are capable of manifesting the character of the extraneous DNA. Examples of such microorganisms include *Escherichia coli* DH1, *Escherichia coli* HB101, *Escherichia coli* W3110, *Escherichia coli* C600, and the like when *Escherichia coli* is used as a host bacterium, Bacillus subtillis 207-25 [Gene, 34, 1-8, (1985)], Bacillus subtillis 207-21 [Journal of Biochemistry, 95, 87-93, (1984)], Bacillus subtillis BD170 [Nature, 293, 481-483, (1981)], Bacillus subtillis M (ATCC6051), and the like when *Bacillus subtillis* is used as a host bacteria, *Saccharomyces cerevisiae* AH-22 [Gene, 39, 117-120, (1985)]. *Saccharomyces cerevisiae* BWG1-7A [Molecular & Cellular Biology, 6, 355-367, (1986)], and the like when *Saccharomyces cerevisiae* is used as a host bacteria.

Introducing the recombinant DNA into the host microorganism may be performed in the presence of calcium ion when the host microorganism is a bacterium belonging to the genus of Escherichia. When a bacterium belonging to the genus of Bacillus is used as a host microorganism, either the competent cell method, protoplast method, or micro-injection method can be used. For the host bacterium belonging to the genus of Saccharomyces the protoplast method or lithium acetate method may be employed.

The transformant bacteria thus obtained, when cultured in a nutrient medium, were found to stably produce a large amount of creatinase. Introducing purposive DNA into the host microorganism can be retrieved by means of detection of the microorganism which can manifest a drug resistance marker of the vector on which the purposive recombinant DNA is held as well as creatinase at the same time. For instance, those bacteria which grow in a selective culture medium of the drug resistance marker and which produce creatinase can be selected.

The recombinant DNA possessing creatinase gene once selected in this manner may be easily extracted from the transformant microorganism for introducing into another host bacterium. Alternatively, a creatinase gene DNA can be digested using a restriction endoneuclease or the like from a recombinant DNA possessing a creatinase gene, and is joined with a vector fragment obtained in a similar manner. The joined DNA—vector fragment is then introduced into the host microorganism.

A creatinase mutein which is a mutant produced by genetic engineering technique from a creatinase gene of this invention possessing substantial creatinase activity can be prepared by amplifying this mutant by the use of various methods, producing the recombinant DNA by inserting the mutant into a vector, and introducing this recombinant DNA into the host microorganism.

The base sequence of the creatinase gene prepared by the method described above was sequenced by the deoxy method [*Science*, 214, 1205–1210 (1981)]. The amino acid sequence of creatinase was determined based on the base sequence.

The method employed in the determination of the amino acid sequence of the portion constituting the N-terminal of the creatinase peptide is now discussed. The creatinase gene-donating microorganism capable of producing creatinase were first cultured in a nutrient medium to produce and accumulate creatinase in the bacteria. The cultured bacteria were collected from the broth by filtration, centrifugation, or the like means. The collected bacteria were then digested either by mechanical means or enzymatic means using lysozyme or the like, and to the digested bacteria were added EDTA and/or a suitable surface active agent, as required, to solubilize creatinase, which was then separated as an aqueous solution. This aqueous solution of creatinase was condensed or subjected to ammonium sulfate fractionation, gel filtration, adsorption chromatography, or ion exchange chromatography to obtain high purity creatinase. The amino acid sequence of the portion constituting the N-terminal of the creatinase peptide was determined on this high purity creatinase using a liquid phase protein sequencer (Beckman System 890ME, manufactured by Beckman, Inc.). In this manner, it was confirmed that the amino acid sequence of said portion is identical to the N-terminal amino acid sequence of the creatinase obtained by genetic engineering technique.

Culturing the transformant host microorganism is conducted under the conditions determined taking the nutrient—physiological characteristics of the host microorganism into consideration. In most of the cases a liquid culturing is employed. In an industrial scale production, however, culturing under deep aerobic stirring is more advantageous. A wide variety of nutrients conventionally used for culturing bacteria can be used for culturing the host microorganism. Specifically, any nutritious carbon compounds can be used as carbon sources, including, for example, glucose, sucrose, lactose, maltose, fructose, molasses, and the like. As nitrogen sources, any available nitrogen compounds can be employed, inclusive of peptones, meat extracts, yeast extracts, casein hydrolysates, and the like. Other ingredients, including salts such as phosphates, carbonates, and sulfates, as well as salts of magnesium, calcium, potassium, iron, manganese, zinc, and the like, and certain types of amino acids or vitamins, may be used as appropriate.

The culturing temperature can be varied in a range in which the bacteria can grow and produce creatinase. The preferable temperature range is 20°–42° C. for the *Escherichia coli*, 30°–37° C. for *Bacillus subtillis*, and 25°–35° C. for *Saccharomyces cerevisiae*. The culturing time may be varied to some degree depending on the culturing conditions. Basically, the culturing is terminated at the time when the yield of creatinase reaches maximum. In usual practice, it takes about 12–48 hours when the host bacterium is *Escherichia coli*, 18–42 hours when the host bacterium is *Bacillus subtillis*, and 24–48 hours when the host bacterium is *Saccharomyces cerevisiae*. It is possible to change the pH of the culture media within the range in which the bacteria can grow and produce creatinase. The especially preferable pH range is 6–8 for *Escherichia coli*, about 7 for *Bacillus subtillis*, and 5–7 for *Saccharomyces cerevisiae*.

Creatinase may be served for use in the form of culture broth as it contains bacteria. The creatinase contained in the culture broth, however, is generally used after separation of the bacteria therefrom by filtration, centrifugation, or the like means. In case creatinase is contained in the bacterial body, the bacteria is first separated by means of filtration or centrifugation. The collected bacteria are then digested either by mechanical means or enzymatic means using lysozyme or the like, and to the digested bacteria are added a chelating agent such as EDTA and/or a suitable surface active agent, as required, to solubilize creatinase, thus collecting creatinase as an aqueous solution.

The solutions containing creatinase thus obtained are then condensed by evaporation in vacuo or by the use of a filter, and subjected to salting-out treatment with ammonium sulfate, sodium sulfate, or the like, or to fractional precipitation using a hydrophilic organic solvent such as methanol, ethanol, acetone, or the like. The precipitate is dissolved into water, and the solution is dialyzed through a semipermeable membrane to eliminate low molecular weight impurities. Alternatively, the precipitate is refined by means of gel filtration, adsorption chromatography, ionexchange chromatography, or the like using an adsorbent or a gel filtration agent. Purified creatinase is produced from the creatinase-containing solution obtained by the use of these various means through vacuum evaporation, lyophilization, or the like.

In the description of this specification, amino acids, peptides, nucleic acids, and nucleic acids-related compounds are abbreviated according to the standard prevailing in the art. Some of the examples of the abbreviation are listed below. Also, all designation of amino acids denote the L-isomers.

DNA: Deoxyribonucleic acid
RNA: Ribonucleic acid
A: Adenine
T: Thymine
G: Guanine
C: Cytosine
Ala: Alanine
Arg: Arginine
Asn: Asparagine
Asp: Aspartate
Cys: Cysyeine
Gln: Gluatmine
Glu: Glutamate
Gly: Glycine
His: Histidine
Ile: Isoleucine
Leu: Leucine
Lys: Lysine
Met: Methionine
Phe: Phenylalanine
Pro: Proline
Ser: Serine
Thr: Threonine
Trp: Tryptophan
Tyr: Tyrosine
Val: Valine Other features of the invention will become apparent in the course of the following description of the exemplary embodiments which are given for illustration of the invention and are not intended to be limiting thereof.

EXAMPLES

EXAMPLE 1

[Preparation of Chromosome DNA]

A chromosome DNA was prepared from strain of Bacillus sp B-0618 (FERM BP-0750) by the following method. The strain was cultured with shaking in 150 ml of a normal bouillon medium containing 0.5% of sodium thiosulfate at 37° C. overnight. The cultured broth was centrifuged at 3,000 rpm for 10 minutes to collect bacterial cells, which was suspended into 5 ml of a solution containing 10% sucrose, 50 mM Tris hydrochloric acid (pH 8.0), and 50 mM EDTA. To the suspension, 1 ml of lysozyme solution (10 mg/ml) was added, and the mixture was incubated at 37° C. for 15 minutes, followed by addition of 1 ml of 10% SDS (sodium dodecylsulfate). To the suspension thus obtained the equal volume of a mixed solvent of chloroform and phenol (1:1) was added, and the mixture was stirred and centrifuged at 10,000 rpm for 3 minutes to separate water and solvent layers. To the separated water layer, 2-fold volume of ethanol was moderately added, and the mixture was stirred slowly with a glass rod so as to cause the DNA wound around the rod. The DNA separated in this manner was dissolved into 10 ml of a solution containing 10 mM Tris hydrochloric acid (pH 8.0) and 1 mM EDTA (such a solution is hereinafter referred to as "TE"). This solution was treated with the equal volume of chloroform—phenol mixed solvent, and was again centrifuged to separate the water layer. To this solution, 2-fold volume of ethanol was further added, and the DNA was again separated from the mixture in the same manner as described above. This finally obtained DNA was dissolved into 2 ml of TE.

EXAMPLE 2

[Preparation of pACYC 184 Plasmid DNA]

*Escherichia coli* pM191 carring pACYC 184 therein [*J. Bacteriol*, 134, 1141 (1981); ATCC37033] was cultured with shaking in 1 liter BHI medium (produced by Difco Co.). When the turbidity of the broth reached $OD_{660}=1.0$, spectinomycin was added to it at a final concentration of 300 μg/ml. Shaking of the broth at 37° C. was continued for at least 16 hours. Upon termination of the shake culturing the broth was centrifuged at 3,000 rpm for 10 minutes to collect bacteria, from which the plasmid DNA was prepared according to the lysozyme—SDS method and the cesium chloride—ethidium bromide method [Maniatis et al, *Molecular Cloning*, 86-94, Cold Spring Harbor (1982)].

EXAMPLE 3

[Construction of Plasmid pCR1 having Creatinase (CR) Gene]

(1) Two (2) μl (about 0.5 μg) of Bacillus sp chromosome DNA prepared in Example 1, 1 μl of 10-fold concentration of Hind III digestion buffer [100 mM Tris hydrochloric acid (pH 7.5), 70 mM $MgCl_2$, 600 mM NaCl, 70 mM mercapto ethanol], 1 μl of Hind III (10 unit/μl; produced by Takara Shuzo Co., Ltd.), and 6 μl of water was mixed and incubated at 37° C. for 1 hour for digestion. Plasmid pACYC 184 DNA (about 0.3 μg) was separately digested using Hind III according to the similar manner. To this was added 0.6 unit of alkaline phosphatase (produced by Takara Shuzo Co., Ltd.; hereinafter referred to as "BAP") and the mixture was incubated at 65° C. for 1 hour. The two DNA solutions thus prepared were mixed together, and to this mixed DNA solution, 0.1 volume of 3M sodium acetate was added. Subsequently, the solution was treated with the equal volume of a chloroform-phenol mixed solvent and centrifuged to separate the water layer. To this the twice amount of ethanol was added, and DNA was precipitated by means of centrifugation and dried in vacuo. The dried DNA was dissolved into 89 μl of water, and to this 10 μl of 10-fold concentration of Leigation buffer [0.5 M Tris hydrochloric acid (pH 7.6), 0.1 M $MgCl_2$, 0.1 M dithiothreitol, 10 mM spermidine, 10 mM ATP) and 1 μl of T4 DNA ligase (175 unit; produced by Takara Shuzo Co., Ltd.) were added and mixed, and the mixture was allowed to stand at 4° C. overnight. This DNA solution was treated with a chloroform-phenol mixture, and the DNA was precipitated by ethanol, dried in vacuo, and dissolved into 10 μl of TE.

(2) *Escherichia coli* DH 1 (Stock No. ME8569; provided by National Gene Research Institute) was cultured in 100 ml of BHI medium (Brain Heart Infusion, produced by Difco Co.), collected at the logarithmic growth phase by centrifugation (10,000 rpm, 2 minutes), and suspended into 40 ml of ice-cooled solution containing 30 mM potassium acetate, 100 mM RbCl, 10 mM $CaCl_2$, 50 mM $MnCl_2$, and 15% glycerin (pH 5.8). After having been allowed to stand at 0° C. for 5 minutes, the suspension was centrifuged to remove the supernatant. The cells were suspended into 4 ml of an ice-cooled solution containing 10 mM MOPS buffer (produced by Dotite Co.), 75 mM $CaCl_2$, 10 mM RbCl, and 15% glycerin (pH 6.5), and the suspension was left at 0° C. for 5 minutes to obtain competent cells.

(3) To 200 μl of the cell suspension 10 μl of the DNA solution prepared in (1) above was added. After the mixture was allowed to stand still at 0° C. for 30 minutes, 1 ml of BHI medium was added to it, and was kept at 37° C. for 90 minutes. An aliquote of the mixture (0.1 ml) was spread on a BHI agar plate containing 25μg/ml of chloramphenicol, and cultured overnight at 37° C. to produce a transformant. This transformant was replicated on a creatinase medium plate (composition: peptone: 5 g, meat extract: 2 g, yeast extract: 5 g, NaCl: 1 g, $K_2HPO_4$: 1 g, $MgSO_4$: 0.5 g, peroxidase: 500 IU, sarcosine oxidase: 500 IU, dianisidine: 0.1 g, creatine: 11.5 g, agar: 15 g, distilled water: 1 liter; pH 7.0), and was further cultured overnight at 37° C..

The periphery of 3 colonies among about 3,000 transformants was colored into charcoal. One of the three strains was named *Escherichia coli* DHI pCR1 (Deposited with Fermentation Research Institute, Agency of Industrial Science and Technology; Deposition No. 9495, FERM P-9495). This strain was cultured after purification in a BHI medium overnight at 37° C. to determine its creatinase productivity according to the creatinase activity measurement method described below. As a result, the creatinase activity was found to be a 0.5 u/ml.

The plasmid contained in the *Escherichia coli* DHI pCR1 strain was separated according to the method described in Example 2, and the plasmid containing a creatinase gene and pACYC 184 gene was named pCR1.

[Measurement of Creatinase Activity]

The creatinase activity was determined by the following method in this invention.

Three solutions were first prepared:

| First Solution: | |
|---|---|
| 0.2M phosphate buffer (pH 7.5) | 0.5 ml |
| 50mM creatine aqueous solution | 4.5 ml |
| Second Solution: | |
| 0.2M Tris hydrochloric acid buffer (pH 8.0) | 0.5 ml |
| 15mM 4-aminoantipyrine aqueous solution | 0.5 ml |
| 0.2% phenol | 0.5 ml |
| peroxidase (50 u/ml) | 0.5 ml |
| sarcosine oxidase (30 u/ml) | 1.0 ml |
| 0.5mM p-chloromercury benzene | 2.0 ml |
| Third Solution: | |
| 0.5mM p-chloromercury benzene | |

A half ml of the first solution was pipetted into a test tube and equilibrated at 37° C. for 3 minutes. To this 10 μl of an enzyme solution was added and maintained at 37° C. for precisely 5 minutes. To the mixture were added 0.5 ml of the third solution and succeedingly 0.5 ml of the second solution. After maintaining this mixture at 37° C. for further 20 minutes, 1.5 ml of distilled water was added and absorbance was measured at a wave length of 500 nm. One unit of the enzyme was defined as the amount to produce 1μ mol of hydrogen peroxide per minute.

EXAMPLE 4

[Mapping of pCR1 and Determination of the Creatinase Gene Base Sequence]

The pCR1 plasmid DNA was prepared from *Escherichia coli* DH1 pCR1 strain in the same manner as described for the preparation of pACYC 184. A pCR1 DNA creavage map was prepared using restriction endoneucleases Cla I, EcoR I, Hind III, Bgl II, Pst I, Sph I (all produced by Takara Shuzo Co., Ltd.), and Ban II (produced by Toyobo Co., Ltd.). The results are shown in FIG. 1. The base sequence of DNA containing creatinase gene was determined according to Dideoxy Method using M13 phage [*Science*, 214, 1205-1210 (1981)]. FIG. 2 shows the base sequence and amino acid sequence of the creatinase gene.

EXAMPLE 5

[Preparation of Creatinase]

*Escherichia coli* DH1 pCR1 was cultured in 20 liters of BHI medium (produced by Difco Co.) through aeration-stirring at 37° C. for 16 hours using a 30-liter jar fermenter. The cultured bacteria were collected by centrifugation at 5,000 rpm for 10 minutes. The creatinase productivity achieved was 5.0 u/ml. The bacteria were washed with 2 liters of physiological saline and suspended into 2 litters of 10 mM phosphate buffer (pH 7.0)

To the suspension thus prepared were added 1 mg/ml of lysozyme chloride and EDTA-2Na (to provide 2 mM concentration). After incubation at 37° C. for 60 minutes with stirring, the mixture was centrifuged at 15,000 rpm for 10 minutes and 1.7 liters of the resulting supernatant was collected.

To the supernatant was slowly added 680 g of ammonium sulfate to salt out a protein precipitate. The precipitate was dissolved into 200 ml of 10 mM phosphate buffer (pH 7.0) and was then subjected to a Sephadex G-25 column for desalting. Subsequently, the desalted solution was subjected to DEAE-Cephallose CL-6B ion exchange chromatography to collect the active fraction. This fraction was desalted and freeze dried to give 4.08 g of a powdery product. The yield achieved was 42%, with the specific activity of the product being 10.3 u/mg.

This invention has clarified the creatinase gene derived from creatinase-producing microorganisms belonging to the genus of Bacillus and the amino acid sequence of the creatinase. In addition, the invention has provided a novel and efficient process for preparing creatinase using the creatinase gene and based on various genetic engineering technique.

Obviously, numerous modifications and variations of the present invention are possible in light of the above teachings. It is therefore to be understood that the scope of the appended claims, the invention may be practiced otherwise than as specifically described herein.

What is claimed as new and desired to be secured by letters patent is:

1. An isolated and purified DNA sequence which encodes the amino acid sequence of a *Bacillus creatinase*, said amino acid sequence starting from the N-terminal having the formula:

A—Gln Gln Ile Thr Asp Leu Glu Arg Thr
Lys Ile Leu Gln Asn Gly Gly Glu Lys Val
Lys Pro Thr Phe Ser Lys Glu Glu Met Thr
Arg Arg Asn Thr Arg Leu Arg Glu Tyr Met
Ala Lys Ala Gly Ile Asp Ala Val Met Phe
Thr Ser Tyr His Asn Ile Asn Tyr Tyr Ser
Asp Phe Leu Tyr Thr Ser Phe Asn Arg Ser
Tyr Ala Leu Val Val Thr Gln Asp Lys His
Val Thr Val Ser Ala Asn Ile Asp Ala Gly
Met Pro Trp Arg Arg Ser Phe Asp Glu Asn
Ile Val Tyr Thr Asp Trp Lys Arg Asp Asn
Phe Leu Tyr Ala Val Lys Lys Val Leu Asn
Glu Gly Gly Phe Ser Ser Gly Arg Leu Gly
Val Glu Asn Asp His Met Thr Leu Asp Leu
Arg Arg Gln Val Gln Asp Ala Leu Pro Asn
Thr Glu Leu Val Asp Val Ser Gln Ala Val
Met Gly His Arg Met Phe Lys Ser Asp Glu
Glu Ile Asp Leu Ile Lys Asn Gly Ala Arg
Ile Ala Asp Ile Gly Gly Ala Ala Val Val
Glu Ala Ile Arg Glu Gly Val Pro Glu Tyr
Glu Val Ala Leu His Gly Thr Glu Ala Met
Val Arg Glu Ile Ala Arg Thr Tyr Pro His
Ala Glu Leu Arg Asp Thr Trp Ile Trp Phe
Gln Ser Gly Ile Asn Thr Asp Gly Ala His
Asn Trp Ala Thr Ser Arg Lys Leu Gln Arg
Gly Asp Ile Leu Ser Leu Asn Cys Phe Pro
Met Ile Ala Gly Tyr Tyr Thr Ala Leu Glu
Arg Thr Leu Phe Leu Glu Glu Val Ser Asp
Arg His Leu Glu Leu Trp Glu Ile Asn Cys
Lys Val His Arg Arg Gly Leu Glu Leu Ile
Lys Pro Gly Ala Arg Cys Met Asp Ile Ala
Ala Glu Leu Asn Glu Ile Tyr Arg Glu His
Asp Leu Leu Ala Asn Arg Thr Phe Gly Tyr
Gly His Ser Phe Gly Val Leu Ser His Tyr
Tyr Gly Arg Glu Ala Gly Leu Glu Leu Arg
Glu Asp Ile Glu Thr Val Leu Glu Pro Gly
Met Val Val Ser Met Glu Pro Met Ile Met
Ile Pro Glu Gly Glu Pro Gly Ala Gly Gly
Tyr Arg Glu His Asp Ile Leu Val Ile Ser
Glu Asn Gly Thr Glu Asn Ile Thr Lys Phe
Pro Phe Gly Pro Glu His Asn Ile Ile Lys
Lys—B wherein A represents an amino acid residue or a hydrogen atom and B represents an amino acid residue or —OH.

2. The DNA sequence of claim 1, which starting from the 5'-end has the formula:

X—CAA CAA ATC ACA GAT CTT GAA AGA ACA
AAG ATT TTA CAA AAC GGC GGG GAG AAA GTA
AAG CCC ACT TTT TCA AAA GAG GAA ATG ACA
CGC CGC AAT ACC CGT TTA CGC GAG TAT ATG
GCG AAG GCC GGA ATC GAT GCT GTT ATG TTC
ACT TCT TAC CAT AAT ATC AAC TAT TAC AGC
GAC TTT TTA TAT ACA TCA TTC AAC AGA TCG
TAT GCG CTC GTC GTC ACT CAG GAC AAG CAT
GTG ACT GTA AGC GCA AAC ATT GAT GCC GGC
ATG CCG TGG AGA CGC AGC TTT GAC GAG AAT
ATT GTT TAC ACA GAC TGG AAA AGA GAC AAC
TTT CTT TAT GCC GTG AAA AAG GTA TTA AAT
GAG GGA GGC TTC TCC AGC GGC CGT CTC GGT
GTA GAA AAT GAT CAT ATG ACG CTG GAT TTA
CGG CGC CAA GTG CAG GAT GCC CTG CCA AAC
ACA GAG CTT GTG GAC GTT TCC CAG GCG GTG
ATG GGG CAT CGG ATG TTT AAG TCT GAC GAG
GAA ATT GAT TTG ATT AAA AAT GGA GCC CGT
ATT GCA GAT ATC GGC GGA GCG GCC GTT GTC
GAA GCG ATT CGC GAA GGC GTA CCG GAA TAC
GAA GTG GCG CTG CAT GGG ACA GAA GCA ATG
GTA CGC GAA ATT GCC CGT ACG TAC CCG CAC
GCT GAA CTT CGG GAC ACG TGG ATT TGG TTT
CAA TCC GGC ATT AAT ACG GAC GGC GCT CAC
AAC TGG GCG ACT TCC CGC AAG CTG CAG CGA
GGA GAT ATT TTG AGC CTA AAC TGC TTC CCG
ATG ATC GCT GGT TAC TAT ACG GCA CTT GAG
CGC ACG TTG TTC TTG GAA GAA GTG TCT GAC
CGC CAT CTT GAA CTG TGG AAA ATC AAC TGT
AAA GTG CAT AGA CGC GGC CTT GAA CTG ATC
AAG CCA GGG GCT AGA TGT ATG GAT ATC GCC

GCT GAA TTA AAT GAG ATC TAC CGC GAG CAC
GAC TTG TTG GCG AAC CGG ACG TTC GGT TAC
GGA CAC TCA TTC GGC GTA CTG AGC CAC TAT
TAC GGA CGT GAG GCT GGA CTG GAG CTG CGG
GAA GAT ATC GAA ACA GTG TTG GAG CCG GGC
ATG GTT GTG TCC ATG GAA CCA ATG ATC ATG
ATT CCA GAG GGA GAG CCG GGA GCG GGC GGT
TAC CGT GAG CAC GAC ATC CTC GTT ATT AGC
GAG AAC GGG ACA GAG AAT ATC ACT AAG TTC
CCA TTC GGT CCG GAG CAT AAC ATT ATT AAA
AAG—Y wherein X represents a codon other than TAA, TAG or TGA, or a hydrogen atom, and Y represents a codon or a hydrogen atom.

3. A transformed microorganism, which comprises the DNA sequence of claim 1.

4. A transformed microorganism which comprises the DNA sequence of claim 2.

5. The transformed microorganism of claim 3, which is a microorganism belonging to the genus of Escherichia.

6. The transformed microorganism of claim 5, which is *Escherichia coli*.

7. A process for preparing a creatinase, comprising:
culturing a transformed microorganism, which comprises the DNA sequence of claim 1.

8. The process of claim 7, wherein said transformed microorganism belongs to the genus Escherichia.

9. The process of claim 7, wherein said transformed microorganism is *Escherichia coli*.

* * * * *